( 12 ) United States Patent
Usiak et al.

(10) Patent No.: US 8,157,850 B2
(45) Date of Patent: Apr. 17, 2012

(54) DEVICE AND METHOD FOR LOADING A LUMINAL GRAFT FOR ENDOLUMINAL DELIVERY

(75) Inventors: Nancy Usiak, Medford, MA (US); Paul DiCarlo, Middleboro, MA (US); Robert F. Rioux, Ashland, MA (US); Kristian DiMatteo, Waltham, MA (US); James Weldon, Roslindale, MA (US); Shubhang Mishra, Southborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1548 days.

(21) Appl. No.: 10/629,077

(22) Filed: Jul. 29, 2003

(65) Prior Publication Data

US 2005/0027349 A1 Feb. 3, 2005

(51) Int. Cl.
*A61F 2/06* (2006.01)
(52) U.S. Cl. .............. 623/1.11; 623/1.12; 623/1.13; 623/1.23
(58) Field of Classification Search .......... 606/108, 606/153, 154, 155, 151; 623/1.12, 1.18, 623/1.22, 1.13, 1.23, 1.27, 1.35, 1.11, 1.3
See application file for complete search history.

(56) References Cited

U.S. PATENT DOCUMENTS

| 5,211,683 | A | 5/1993 | Maginot | |
|---|---|---|---|---|
| 5,290,295 | A | 3/1994 | Querals et al. | |
| 5,591,197 | A | 1/1997 | Orth et al. | |
| 5,662,700 | A | 9/1997 | Lazarus | |
| 5,676,697 | A | 10/1997 | McDonald | |
| 5,723,003 | A * | 3/1998 | Winston et al. | 623/1.13 |
| 5,755,770 | A * | 5/1998 | Ravenscroft | 623/1.13 |
| 5,824,040 | A * | 10/1998 | Cox et al. | 623/1.35 |
| 5,968,053 | A | 10/1999 | Revelas | |
| 6,015,422 | A | 1/2000 | Kerr | |
| 6,063,112 | A * | 5/2000 | Sgro | 623/1.12 |
| 6,090,136 | A | 7/2000 | McDonald et al. | |
| 6,254,628 | B1 * | 7/2001 | Wallace et al. | 623/1.12 |
| 6,328,727 | B1 | 12/2001 | Frazier et al. | |
| 6,334,867 | B1 * | 1/2002 | Anson | 623/1.13 |
| 6,352,553 | B1 * | 3/2002 | van der Burg et al. | 623/1.23 |
| 6,361,637 | B2 * | 3/2002 | Martin et al. | 156/187 |
| 6,398,802 | B1 | 6/2002 | Yee | |
| 6,416,536 | B1 | 7/2002 | Yee | |
| 6,475,166 | B1 | 11/2002 | Escano | |
| 6,520,986 | B2 * | 2/2003 | Martin et al. | 623/1.13 |
| 6,669,719 | B2 * | 12/2003 | Wallace et al. | 623/1.12 |
| 6,814,747 | B2 * | 11/2004 | Anson et al. | 623/1.13 |
| 6,827,731 | B2 * | 12/2004 | Armstrong et al. | 623/1.12 |
| RE39,335 | E * | 10/2006 | Anson | 623/1.13 |
| 2002/0082674 | A1 * | 6/2002 | Anson et al. | 623/1.13 |
| 2004/0215320 | A1 * | 10/2004 | Machek | 623/1.13 |

FOREIGN PATENT DOCUMENTS

WO WO 9709007 A1 * 3/1997

OTHER PUBLICATIONS

Andrew Kerr et al.; "Slimgraft: A Percutaneious Endovascular Graft System," J. Endovasc. Ther., 2000; 7: 41-46.

* cited by examiner

*Primary Examiner* — Gary Jackson
*Assistant Examiner* — Michael Mendoza
(74) *Attorney, Agent, or Firm* — Brooks, Cameron & Huebsch, PLLC

(57) ABSTRACT

An endoluminal graft is wrapped axially upon itself to form a low profile, which facilitates endoluminal delivery. Apparatus and systems for making and using such grafts are also disclosed.

5 Claims, 4 Drawing Sheets

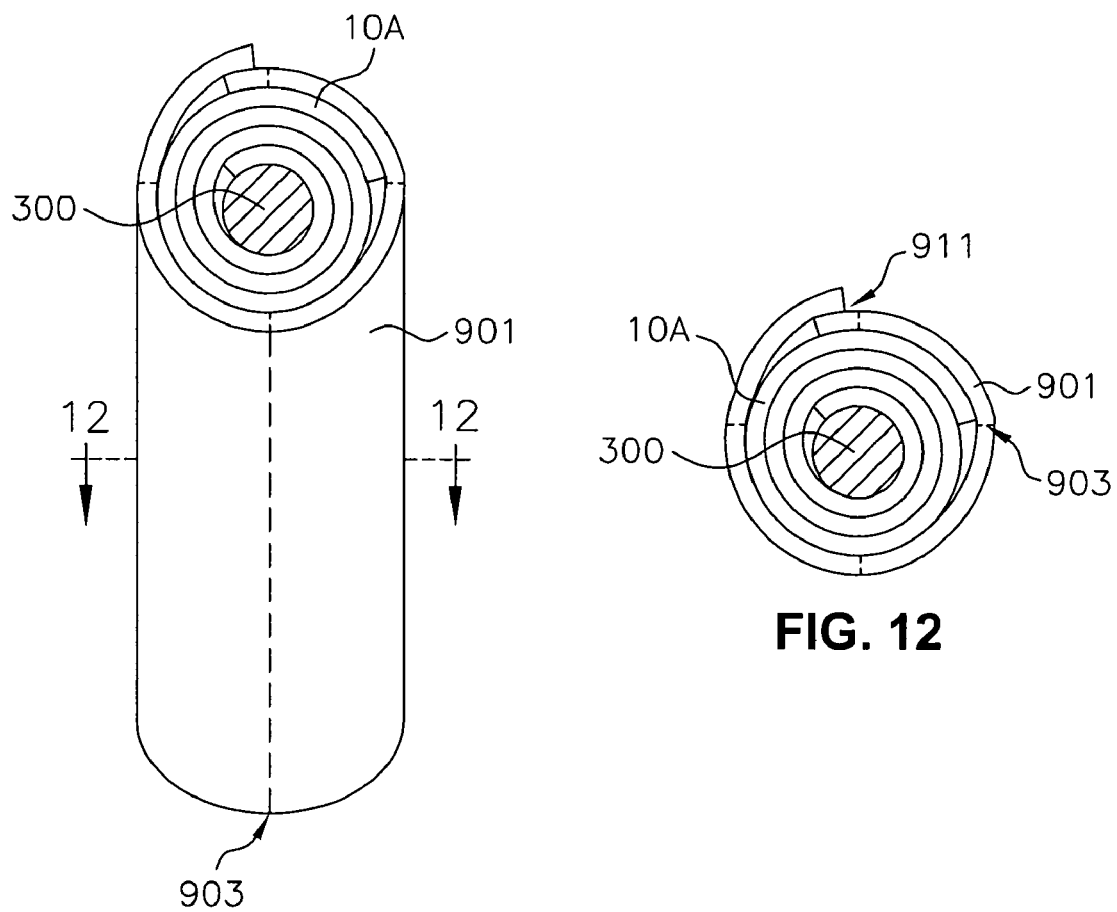
FIG. 12
FIG. 11
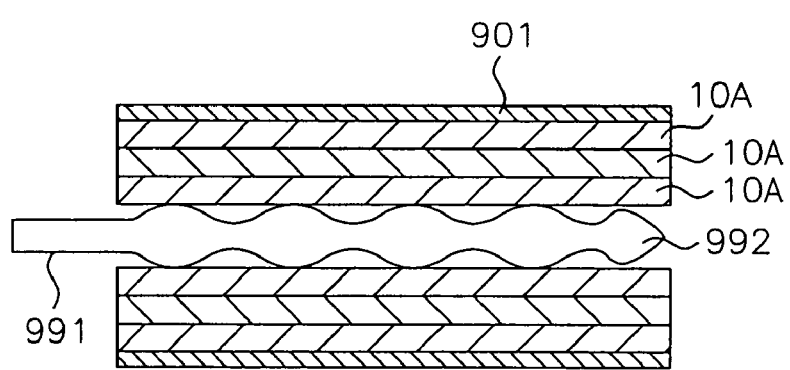
FIG. 13

DEVICE AND METHOD FOR LOADING A LUMINAL GRAFT FOR ENDOLUMINAL DELIVERY

TECHNICAL FIELD

This invention relates to an apparatus and method for preparing a luminal graft for endoluminal delivery, and particularly for providing a luminal graft with a low profile for endoluminal delivery.

BACKGROUND OF THE INVENTION

Luminal or tubular grafts are placed in native blood vessels and other body lumens to treat various medical conditions, including aneurysms and stenoses. Open surgical procedures can be used to implant such grafts. These procedures, however, can be traumatic for patients and require an extended recovery period. Another approach is to deliver a graft endoluminally through an access or cut down in a vessel remote from the intended graft location. Endoluminal delivery is typically less traumatic for patients than open surgery and requires a shorter recovery period. Endoluminal delivery, however, can be difficult where native vessels provide a tortuous path for delivery. Also, remote vessels typically provide small openings, which may not be large enough to accept an existing graft and delivery system. To overcome the shortcomings of existing grafts and delivery systems, a need exists for a low profile graft configuration for endoluminal delivery.

SUMMARY OF THE INVENTION

To meet these and other needs, and in view of its purposes, the present invention comprises an apparatus and method for rolling a luminal graft about itself into a low profile configuration suitable for deployment through a catheter from an access in a body lumen to a location remote therefrom. For this purpose, two cylindrical rollers are rotationally mounted on parallel axes. A continuous belt is disposed on the rollers to form an inner loop defining a pocket and an outer loop circumscribing the rollers and the inner loop. A mandrel is disposed within the pocket to maintain the pocket and press the graft against the belt. A tensioning device applies tension to the belt. One of the cylinders is rotated about its axis to roll the graft onto the mandrel.

More generally, the invention comprises an endoluminal graft system including a graft rolled up on its longitudinal axis to provide a low profile for delivery through a catheter, and apparatus and methods for making and using a low profile graft. Varied rolled grafts may be provided in a kit for selection and use during a surgery.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features may be arbitrarily expanded or reduced for clarity. Included in the drawing are the following figures:

FIG. 11 is a perspective view of a rolled graft restrained by a temporary covering according to an exemplary embodiment of the present invention;

FIG. 12 is a sectional view of the rolled graft of FIG. 12 taken generally in the plane 12-12 in FIG. 11;

FIG. 13 is a schematic view partially in cross-section, of a rolled graft loaded onto a delivery catheter according to an exemplary embodiment of the present invention.

DETAILED DESCRIPTION OF THE INVENTION

Figures 1, 2:
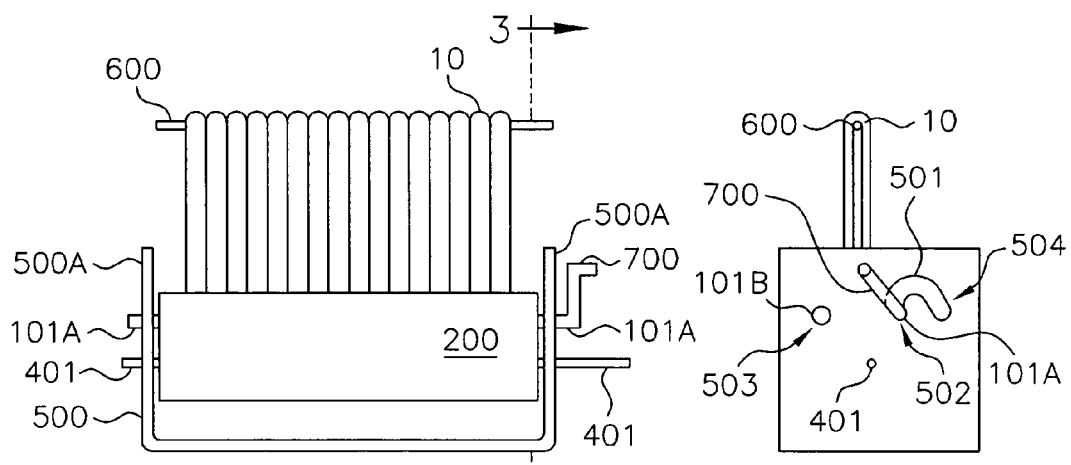
FIG. 1 shows an apparatus for rolling a luminal graft into a low profile configuration according to an exemplary embodiment of the present invention.
FIG. 2 is an end view of the apparatus of FIG. 1.

Referring now to the drawings, in which like reference numbers refer to like elements throughout, FIGS. 1-2 show an exemplary embodiment of an apparatus for rolling a luminal graft into a low profile configuration.

Figures 3A, 3B:
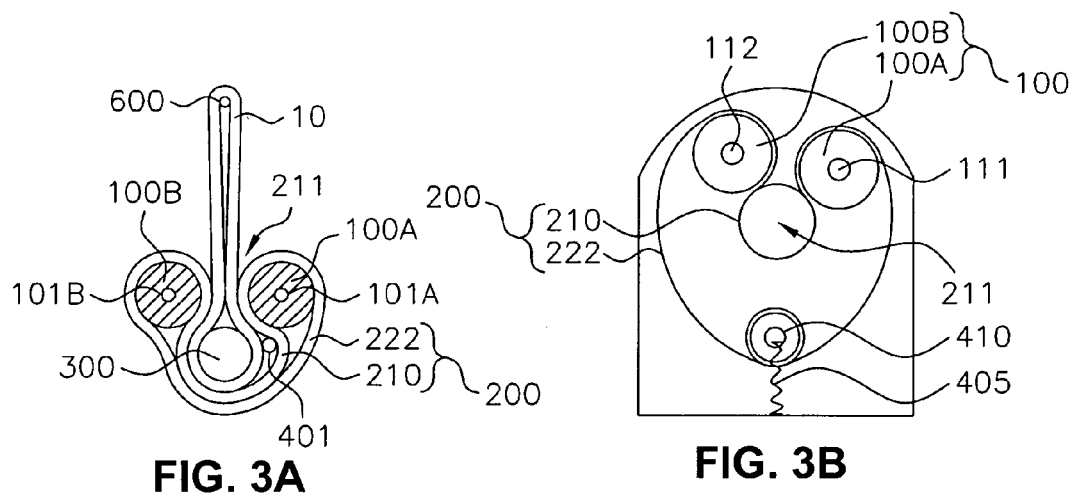
FIG. 3A is a sectional view of an exemplary embodiment of the apparatus of FIG. 1 in the plane 3-3 in FIG. 1.
FIG. 3B sectional view of an alternative embodiment of the apparatus of FIG. 1 in the corresponding plane 3-3 of the alternative embodiment.

Referring now to FIGS. 1, 2, and 3A, an exemplary embodiment of an apparatus is shown for rolling a luminal graft 10 (in this case a circumferentially ribbed graft) having a tubular cross-section in its deployed configuration, but collapsed for present purposes into a planar cross-section, into a low profile configuration according to an exemplary embodiment of the present invention. The axis of the luminal graft is parallel to tensioning bar 600, which supports the graft 10 as it is introduced into the apparatus shown. In this apparatus, a frame 500 is provided having two generally vertical sides 500A extending upwardly from each end of a generally horizontal portion. This frame may comprise, for example, molded plastic. Two cylindrical rollers (100A, 100B in FIG. 3A) are rotationally mounted on parallel axes by tabs 101A, 101B. As shown in FIG. 2, various openings are formed in each of the sides of frame 500. A hole 503 and a curved (or J-shaped) slot 501 are positioned in sides 500A to receive tabs 101A, 101B. Slot 501 has a closed end 502 closest to the hole for tab 101B, a raised middle portion, and an open end 504 farthest from the hole for tab 101B. Closed end 502 curves away from the hole for tab 101B to provide a hard stop to restrain tab 101A and the associated roller. Another hole is positioned in sides 500A below hole 503 and slot 501 to receive a tension rod 401. A crank 700 may optionally be formed integral with tab 101A for turning tab 101A and its associated roller (100A in FIG. 3A) operatively connected to tab 101A to roll the graft.

A leading edge of collapsed graft 10 is introduced between the two rollers (100A, 100B in FIG. 3A). A belt 200 is disposed on the rollers. Belt 200 has excess length when disposed on the rollers, and forms a pocket (211, best seen in FIG. 3B) between the rollers. Preferably, optional graft tension rod 600 restrains graft 10 at its trailing edge to maintain tension in the collapsed or flattened graft.

Referring now to FIG. 3A, in which graft 10 and portions of the rolling apparatus are shown in cross-section, rollers 100A, 100B rest within sides 500A of frame 500 and have a length greater than graft 10. These rollers may comprise any material having sufficient strength and providing a surface finish capable of imparting sufficient frictional force to roll graft 10. A continuous belt 200 is disposed on rollers 100A,100B. Belt 200 has a width greater than the length of graft 10 and no greater than the length of the rollers. The length of belt 200 is sufficient to form an inner loop 210 and an outer loop 222 when belt 200 is disposed on rollers 100. Belt 200 passes between rollers 100 and defines a pocket 211 in inner loop 210. Outer loop 222 circumscribes rollers 100 and inner loop 210. As shown in FIG. 3A, pocket 211 is open to the exterior of outer loop 222 between rollers 100A, 100B.

Typically, mandrel is operatively connected to graft 10 and disposed within pocket 211 to maintain the pocket and press graft 10 against belt 200. The mandrel may be disposed within the inner surface of graft 10 as shown in FIG. 3A. Graft 10 may alternatively be flattened and rolled or fastened onto the mandrel with its outside surface contacting the mandrel. In an exemplary embodiment of the invention, as shown in FIG. 3, the mandrel comprises a floating pin mandrel 300 having a cylindrical shape, as shown in FIG. 3A. This floating pin mandrel 300 has a length about equal to the width of graft 10.

Alternatively, the mandrel may be a portion of a delivery system used to deliver graft 10 to a desired location in a patient's vascular system. For example, the mandrel may be a catheter, which is guided through a patient's native vessels from a cut-down remote from the ultimate graft location or a portion of a catheter. The mandrel may also be a guide wire with graft 10 rolled directly onto it.

In operation, roller 100A is rotated about its axis, imparting motion to belt 200 through frictional contact. Belt 200 in turn imparts rotational force to the portion of graft 10 disposed in pocket 211 and operatively associated with mandrel 300. This rotational force is applied through frictional contact between belt 200 and graft 10. A graft tension rod 600 may be introduced into graft 10 at its trailing end while it is rolled. Graft tension rod 600 is biased away from pocket 211 and maintains uniform tension along the length of graft 10 to prevent wrinkles in graft 10. Uniform tension in graft 10 also allows graft 10 to be rolled tighter (i.e., with a lower profile) than a graft rolled without tension.

A belt tensioning device maintains tension in belt 200. This belt tensioning device may be a removable tension rod 401 as shown in FIGS. 1, 2, and 3A. Tension rod 401 applies tension to belt 200 by expanding pocket 211. Tension rod 401 also helps to tuck the portion of graft 10 disposed around mandrel 300 under the portion of graft 10 extending from mandrel 300 to begin rolling graft 10 onto itself. Tension rod 401 may be removed from pocket 211 after graft 10 is partially rolled onto mandrel 300. After graft 10 is partially rolled, the increased size of rolled graft 10 provides tension in belt 200.

Alternatively, the tensioning device may be a biasing device, such as a tensioning spring 405 as shown in FIG. 3B. The biasing device applies tension to belt 200 through a roller 410 or rod disposed inside of outer loop 222 and outwardly biases outer loop 222. By outwardly biasing outer loop 222, biasing device 405 applies tension to belt 200, minimizing the size of pocket 211 in inner loop 210 to enable rolling of graft 10.

In an exemplary embodiment of the invention, the rolling device described above is loaded with graft 10 and mandrel 300. First, floating pin mandrel 300 is placed inside of graft 10. Then, first roller 100A is positioned at an open position providing access to pocket 211 by moving tab 101 of roller 100A in a slot 501 to a distant position 504. Next, the portion of graft 10 containing floating pin mandrel 300 is placed into pocket 211, and tension rod 401 is positioned in holes in frame 500 so that it traverses pocket 211. Then, first roller 100A is positioned in a closed position by moving tab 101 to close position 502.

After the rolling device is loaded, roller 100A is rotated about its axis, imparting motion to belt 200 and creating frictional force acting on graft 10. This frictional force causes graft 10 to roll onto itself to form a rolled graft, which is described hereafter. Graft 10 maintains a consistent length while it is rolled, because it is not subjected to radial or axial force. In the rolled or low-profile configuration, graft 10 may have a diameter on the order of 6-28 French (depending on the graft). This low profile enhances a surgeon's ability to deliver graft 10 to an intended graft location through tortuous vascular anatomy.

As described above, in the low profile configuration, graft 10, which is tubular in shape, is flattened against itself and wrapped or rolled around itself onto a mandrel 300. Floating pin mandrel 300 may be removed to provide a rolled graft with a central opening. Alternatively, the mandrel may remain within the rolled graft and function as a part of a delivery system for the graft.

Optionally, roller 100A may be biased toward roller 100B to provide uniform pressure when a rolling device is used to roll grafts having different thicknesses. Roller 100A may be biased by a spring device or other means known in the art. A hard stop may be provided to prevent excess separation of roller 100A from roller 100B. Thus, the gap between rollers 100 can vary to accommodate the particular graft being used.

Figure 4:
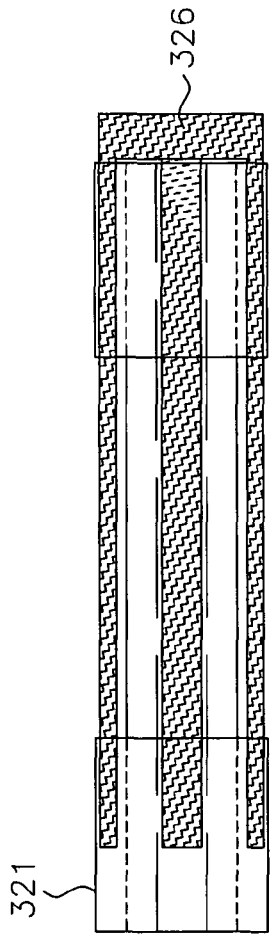
FIG. 4 shows a locking pin assembly for use as a mandrel according to an exemplary embodiment of the present invention.
Figure 5:
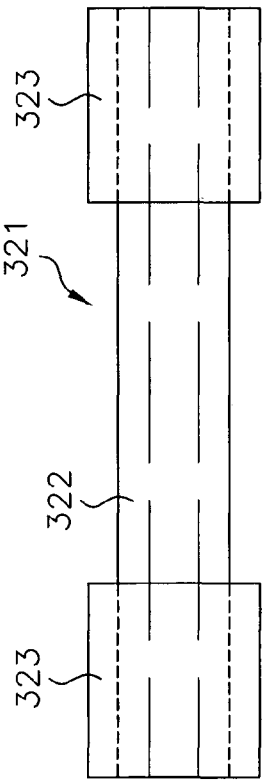
FIG. 5 shows a pin component of the locking pin assembly of FIG. 4.
Figure 6:
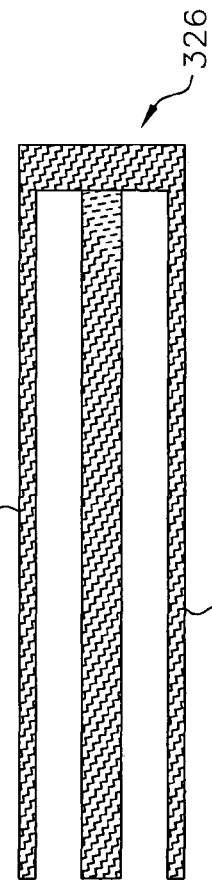
FIG. 6 shows a lock component of the locking pin assembly of FIG. 4.
Figure 7:
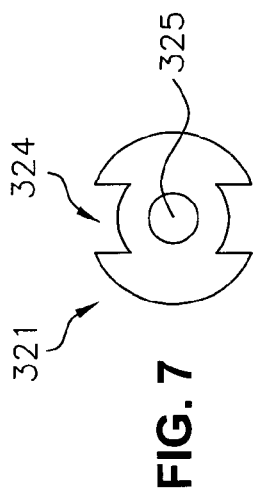
FIG. 7 is an end view of the pin component of FIG. 5.
Figure 8:
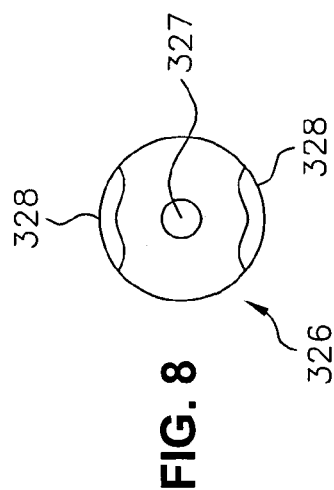
FIG. 8 is an end view of the lock component of FIG. 7.

According to an exemplary embodiment of the present invention, the mandrel on which graft 10 is rolled, may be a locking pin assembly 320, as shown in FIG. 4. Locking pin assembly 320 comprises a pin component 321 and a lock component 326. Pin component 321 has a stepped generally cylindrical profile, as shown in FIG. 5. A recessed portion 322 is disposed between two end portions 323. At least one end portion 323 is removable to allow graft 10 to slide off pin 320. As shown in FIG. 6, one or more grooves 324 are provided in end portions 323, and an aperture 325 extends longitudinally through pin 321. The graft (not shown) is rolled onto recessed portion 322. Lock component 326, shown in FIGS. 7, 8, comprises a shaft 327 configured to fit into aperture 325 connected at one end to fingers 327 configured to fit into grooves 324 and provide atraumatic restraint to the rolled graft. Locking pin 320 tucks the graft under its trailing portion and facilitates tighter rolling, and therefore, a lower profile. Locking pin 320 is removed after rolled graft 10A is secured by a temporary covering, a tether, or the like. To remove locking pin 320, lock 326 is axially extracted from pin 321. Locking pin 320 may be locked to graft 10 with pin 321 contacting an external surface of graft 10.

In yet another embodiment, the crank may comprise an electric motor (not shown). The electric motor can be configured to rotate crank 700 (in FIG. 2) to enable automatic compression and rolling of the graft. Thus the graft may be precisely and efficiently loaded by activating the motor, and not subject to variable pressure typical of manual rotation.

Figure 9:
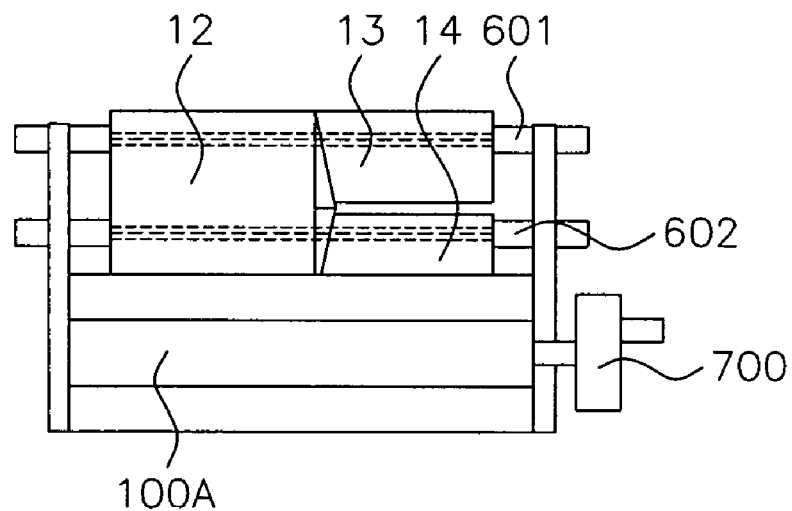
FIG. 9 shows a bifurcated graft loaded onto two tension rods for rolling into a low profile configuration using an apparatus according to an exemplary embodiment of the invention.

The apparatus of the present invention may be used to roll a bifurcated graft into a low profile configuration, as shown in FIG. 9. This apparatus operates in a manner similar to the apparatus illustrated in FIGS. 1-3 and described above. Instead of single graft tension rod 600, however, two graft tension rods 601, 602 are used. The bifurcate graft comprises a main body 12 in communication with first and second limbs 13,14. First graft tension rod 601 is placed inside of main body 12 and first limb 13 to apply tension during rolling. Second graft tension rod 602 is placed inside of second limb 14 to apply tension during rolling. As each graft tension rod approaches rollers 100A, 100B, it is removed from the graft.

Figure 10:
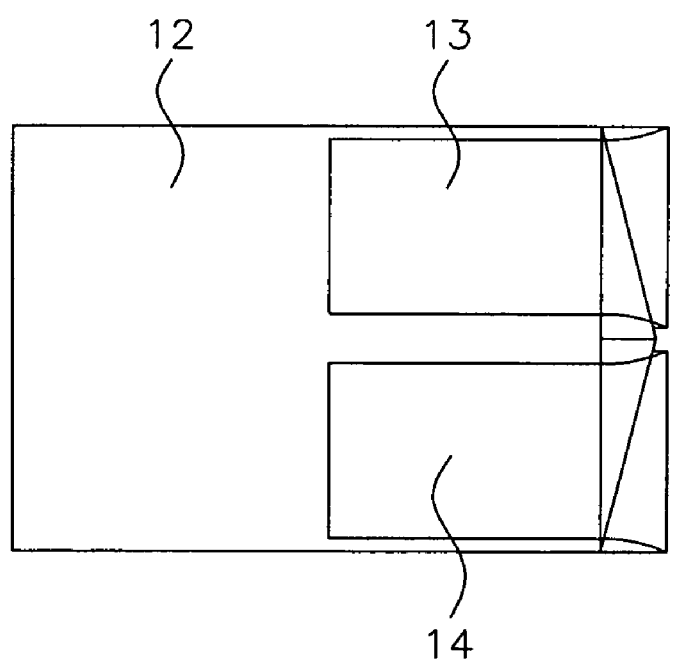
FIG. 10 shows a bifurcated graft with both legs eversed into the trunk for rolling into a low profile configuration using an apparatus according to an exemplary embodiment of the invention.

Referring now to FIG. 10, there is shown an alternative collapsed configuration of a bifurcated graft, in which limbs 13,14 may be folded inside main body 12 prior to rolling the graft. This method of preparing a graft for delivery provides a rolled graft having a shorter length, which facilitates delivery through tortuous native vessels. Upon deployment, limbs 13,14 may be removed from main body 12 in-situ by everting them, using, for example, snares or tethers.

Referring now to FIG. 11, there is shown one form of a rolled graft, suitable for deployment, in accordance with the present invention. In accordance with one method of producing this form of the invention, a temporary covering 901 may be placed around graft 10 after it is rolled to radially restrain graft 10 in a low-profile, rolled configuration. After graft 10 is fully rolled into a cylinder, a leading edge of a temporary covering 901 is introduced into the pocket (211 in FIG. 3A) of the rolling device. Roller (100A in FIG. 3A) is then further rotated causing the temporary covering to roll onto graft 10. An adhesive is applied to the trailing end of the covering such that covering adheres to itself, restraining graft 10 in the rolled state as rolled graft 10A. After temporary covering is in place, rolled graft 10A may be removed from the pocket of the rolling apparatus, and mandrel 300 may optionally be removed from rolled graft 10A. Alternatively, the mandrel may be a portion of a delivery system such as a catheter or a guide wire.

As shown in FIGS. 11 and 12, rolled graft 10A may be restrained by a temporary covering 901 disposed radially outward of rolled graft 10A. Temporary covering 901 may, for example, comprise a polymer sheet having a low-tack adhesive 911 applied to one of its ends. The temporary covering 901 is rolled onto rolled graft 10A such that the trailing end having adhesive 911 on it overlaps the leading end of temporary covering 901, adhering the leading end and trailing end of temporary covering 901 together.

As shown in FIGS. 11 and 12, temporary covering 901 may have perforations 903 to create weakened regions that will tear when outward force is applied to rolled graft 10A. Alternatively, temporary covering may comprise absorbable material which is absorbed while temporary covering is in the delivery system in a patient's body, or a material which is dissolved after rolled graft is placed within a delivery system, before placement in a patient's body. Temporary covering 901 may alternatively be removed by mechanical means, such as a drawstring or ribbon embedded in the temporary covering which tears or unravels the temporary covering when pulled.

Referring again to FIGS. 1-3A, the rolled graft is removed from the rolling device, by positioning roller 100A at an open position providing access to pocket 211. Tab 101 of roller 100A in slot 501 is moved to distant position 504. Rolled graft 10A is then removed from pocket 211. Floating pin mandrel 300 may next be removed from the rolled graft and the rolled graft may be loaded onto a delivery catheter (not shown) or captured within a delivery catheter, with or without a core mandrel or guide wire mounted axially within the rolled graft (also not shown).

In the alternative form of the invention including a temporary covering on the rolled graft, the temporary covering may be removed when rolled graft 10A is loaded into a delivery sheath. In another optional application, the temporary covering may be used in place of a sheath and be removed in-situ. In yet another optional application, the covering may be bioabsorbable, and be absorbed in the patient.

In an exemplary embodiment of the invention, a plurality of differing grafts 10 is provided in a kit. The plurality of grafts may differ in size (e.g., diameter, length, etc.), type (e.g., stent graft, unsupported graft, etc.), or both size and type. The plurality of grafts 10 may be in a rolled configuration or an unrolled configuration. Each graft in the kit is compatible with a low profile delivery system, which may be provided in the kit. This provides the physician with the option to assess a patient's native vessels during or just prior to an endoluminal procedure to determine the optimal graft for the patient. The selected graft is rolled after selection, or alternatively, may be kitted in the rolled configuration. Then the selected graft is mounted on the delivery catheter by placing the delivery catheter into an opening in rolled graft 10A left by removal of mandrel 300. If the plurality of grafts in the kit is in an unrolled configuration, an apparatus for rolling the selected graft is also provided in the kit.

Referring now to FIG. 13, there is shown a rolled graft 10A loaded into a delivery system, comprising a catheter 991 having an expansion device 992. In an exemplary embodiment of the invention, expansion device 992 comprises a balloon as shown in FIG. 13. Alternatively, an expansion device may comprise a self-expanding spring. In still another exemplary application, rolled graft 10A may comprise a self-expanding stent attached to the graft and onto which the graft is mounted axially. In this application, the self-expanding stent is rolled with the graft. The attached self-expanding stent may be used in conjunction with or independently of expansion device 992.

Rolled graft 10A may be placed on expansion device 992 by threading catheter 991 and expansion device 992 through the opening in rolled graft 10A left by removing floating pin mandrel 300. Alternatively catheter 991 and expansion device 992 may be used as the mandrel, so that rolled graft 10A is rolled directly onto catheter 991 and expansion device 992. As shown in FIG. 13, rolled graft 10A may be radially restrained in a rolled configuration by temporary covering 901. Alternatively, a delivery sheath (not shown) may be disposed over catheter 991, expansion device 992, and rolled graft 10A. This delivery sheath is axially movable relative to catheter 991 and may be configured to abut a lumen expanding nosecone during delivery of rolled graft 10A through a body lumen.

Referring again to an expansion device 992 comprising a balloon, expansion device 992 is in fluid communication with an inflation lumen (not shown) disposed in catheter 991. Rolled graft 10A may be pressed onto the balloon or temporarily attached to the balloon using sutures, adhesive, a retaining member, or the like. An inner sheath (not shown) may optionally be disposed between expansion device 992 and rolled graft 10A. This optional inner sheath may facilitate rolling graft 10 directly thereon, and may be used to restrain expansion member after the graft is fixed to the lumen wall.

In use, rolled graft 10A is advanced endoluminally from an access remote from a desired graft location to the desired location on catheter 991. A guide wire (not shown) may be used to guide catheter 991. Rolled graft 10A may be held on delivery catheter 991 by temporary covering 901 or by a sheath 996 (not shown) positioned over rolled graft 10A. After rolled graft 10A is advanced to the desired location, temporary covering 901 is removed from rolled graft 10A, and rolled graft 10A is expanded using expansion device 992 or, alternatively through self-expansion, as described above. Temporary covering 901 may be removed by pulling a rip cord or a ribbon to tear or unravel temporary covering 901. Alternatively, temporary covering may comprise weakened areas, which fail when expansion device 992 is expanded. In another alternative, part or all of temporary covering 901 may comprise absorbable material and fail through absorption.

To expand the expansion device 992 shown in FIG. 13, the balloon is inflated to apply radially outward force on rolled graft 10A. This outward force causes rolled graft 10A to unroll and expand against the wall of the lumen in which it is disposed. Alternative expansion devices, such as spring devices, or self-expansion may also be used to apply this radially outward force to rolled graft 10A.

After expansion, graft 10 may be fixed to the lumen wall using fixation devices such as staples, sutures, or other means known in the art. Fixation devices may be delivered either endoluminally or laproscopically. Alternatively, graft 10 may be anchored to the lumen wall by anchors or the like attached to graft 10 or integral with graft 10. After fixation, the balloon is deflated. Then expansion device 992 is withdrawn from the patient with catheter 991. In an alternative application, the outward force from a self-expanding stent integral with graft 10 is sufficient to fix the graft to the lumen wall.

Although illustrated and described above with reference to certain specific embodiments, the present invention is not intended to be limited to the details shown. Rather, various modifications may be made in the details within the scope and range of equivalents of the claims and without departing from the invention.

What is claimed:

1. A rolled graft and a delivery system, comprising a generally tubular graft flattened against itself and rolled onto itself into a cylindrical configuration, wherein said graft includes a larger diameter main section and two smaller diameter sections that terminate the main section at an axial end of said larger diameter section, wherein the two smaller diameter sections are both disposed within the terminated axial end of the main section to enable a length of said rolled graft to be shortened during delivery by the delivery system inside a body lumen, in combination with an expansion element disposed axially within said rolled graft, further comprising a temporary covering surrounding and restraining said graft in said cylindrical configuration, wherein said temporary covering is configured to be released when the rolled graft is within the delivery system.

2. The rolled graft of claim 1 further comprising an aperture extending along an axis of said cylindrical rolled graft.

3. The rolled graft of claim 1 wherein said graft is rolled onto an axial member.

4. The rolled graft of claim 1 wherein said temporary covering is absorbed after delivery into a body lumen.

5. A rolled graft and a delivery system, comprising a generally tubular graft flattened against itself and rolled onto itself into a cylindrical configuration, wherein said graft includes a larger diameter main section and two smaller diameter sections that terminate the main section at an axial end of said larger diameter section, wherein the two smaller diameter sections are both disposed within the terminated axial end of the main section to enable a length of said rolled graft to be shortened during delivery by the delivery system inside a body lumen, further comprising a temporary covering surrounding and restraining said graft in said cylindrical configuration, wherein said temporary covering is configured to be dissolved or absorbed when the rolled graft is within the delivery system.

\* \* \* \* \*